United States Patent
Ng et al.

(10) Patent No.: US 10,145,767 B2
(45) Date of Patent: Dec. 4, 2018

(54) SLIDE STAINING ASSEMBLY AND COVER MEMBER

(71) Applicant: LEICA BIOSYSTEMS MELBOURNE PTY LTD, Mt Waverley, Victoria (AU)

(72) Inventors: Kenneth Heng-chong Ng, Donvale (AU); Mark Brian Dockrill, Chadstone (AU); Peter Toogood, Vermont (AU); Martin Limon, Richmond (AU); Daniel Dobrogorsky, St. Albans (AU); Mark Wilcock, Parkdale (AU); Greg Boyes, Croydon (AU); Brendyn Rodgers, Blackburn (AU); Stephen John Bagnato, Mt Waverley (AU); Ashan Chiranga Perera, Richmond (AU)

(73) Assignee: LEICA BIOSYSTEMS MELBOURNE PTY LTD, Mount Waverly, Victoria (AU)

( * ) Notice: Subject to any disclaimer, the term of this patent is extended or adjusted under 35 U.S.C. 154(b) by 0 days.

(21) Appl. No.: 14/439,867

(22) PCT Filed: Nov. 1, 2013

(86) PCT No.: PCT/AU2013/001267
§ 371 (c)(1),
(2) Date: Apr. 30, 2015

(87) PCT Pub. No.: WO2014/066950
PCT Pub. Date: May 8, 2014

(65) Prior Publication Data
US 2015/0253225 A1 Sep. 10, 2015

Related U.S. Application Data

(60) Provisional application No. 61/721,280, filed on Nov. 1, 2012.

(51) Int. Cl.
*G01N 1/00* (2006.01)
*G01N 1/31* (2006.01)
*B01L 3/00* (2006.01)

(52) U.S. Cl.
CPC .............. *G01N 1/312* (2013.01); *B01L 3/502* (2013.01); *G01N 1/31* (2013.01);
(Continued)

(58) Field of Classification Search
CPC .................................... G01N 1/00; B01L 3/00
See application file for complete search history.

(56) References Cited

U.S. PATENT DOCUMENTS

| 5,188,963 A | 2/1993 | Stapleton |
| 5,346,672 A * | 9/1994 | Stapleton .............. B01L 3/5027 422/559 |

(Continued)

FOREIGN PATENT DOCUMENTS

| JP | H05-501647 A | 4/1993 |
| JP | H11-502926 A | 3/1999 |

(Continued)

OTHER PUBLICATIONS

International Search Report for PCT/AU2013/001267 dated Jan. 13, 2014 [PCT/ISA/210].

(Continued)

*Primary Examiner* — Jyoti Nagpaul
(74) *Attorney, Agent, or Firm* — Sughrue Mion, PLLC

(57) ABSTRACT

A sample processing assembly for treatment of a sample on a substrate includes a mounting surface for the substrate and a closure body configured to releasably retain a cover member. The closure body is movable between an open position and a substantially closed position. When a substrate is placed in the assembly and the closure body is in the substantially closed position while retaining a cover mem- (Continued)

ber, a reaction chamber is formed for processing a sample. A cover member for use with the sample processing assembly is also provided.

19 Claims, 10 Drawing Sheets

(52) U.S. Cl.
CPC ... *B01L 2300/043* (2013.01); *B01L 2300/047* (2013.01); *B01L 2300/0609* (2013.01); *B01L 2300/0809* (2013.01)

(56) References Cited

U.S. PATENT DOCUMENTS

| | | | |
|---|---|---|---|
| 5,687,870 A * | 11/1997 | Carlile | F16J 13/24 220/316 |
| 6,258,593 B1 | 7/2001 | Schembri et al. | |
| 6,272,939 B1 * | 8/2001 | Frye | B01L 3/0203 73/864.81 |
| 6,673,620 B1 * | 1/2004 | Loeffler | B01L 3/502 359/398 |
| 7,220,573 B2 | 5/2007 | Shea et al. | |
| 7,247,497 B2 | 7/2007 | Dahm et al. | |
| 2001/0003652 A1 | 6/2001 | Freeman | |
| 2003/0059349 A1 | 3/2003 | Howe | |
| 2004/0086428 A1 | 5/2004 | Loeffler et al. | |
| 2012/0149050 A1 | 6/2012 | Lapen et al. | |
| 2014/0004561 A1 | 1/2014 | Lapen et al. | |
| 2014/0315256 A1 | 10/2014 | Dockrill et al. | |

FOREIGN PATENT DOCUMENTS

| | | |
|---|---|---|
| JP | 2003-530545 A | 10/2003 |
| JP | 2013-545981 A | 12/2013 |
| JP | 2014-533823 A | 12/2014 |
| WO | 2013/071352 A1 | 5/2013 |

OTHER PUBLICATIONS

Extended European Search Report dated Jun. 10, 2016 in European Application No. 13851664.6.
Communication dated Jun. 10, 2016 from the European Patent Office in counterpart application No. 13851664.6.
State Intellectual Property Office of P. R. China, Office Action dated Dec. 6, 2016 issued in a corresponding Chinese Application No. 201380069047.7.
Patent Examination Report No. 1 dated Nov. 28, 2016.
Examination Report No. 2 dated Jan. 23, 2017.
Communication dated Aug. 22, 2017, from Japanese Patent Office in counterpart application No. 2015-540002.
Japanese Office Action; Application No. 2015-540002; dated Apr. 17, 2018.

* cited by examiner

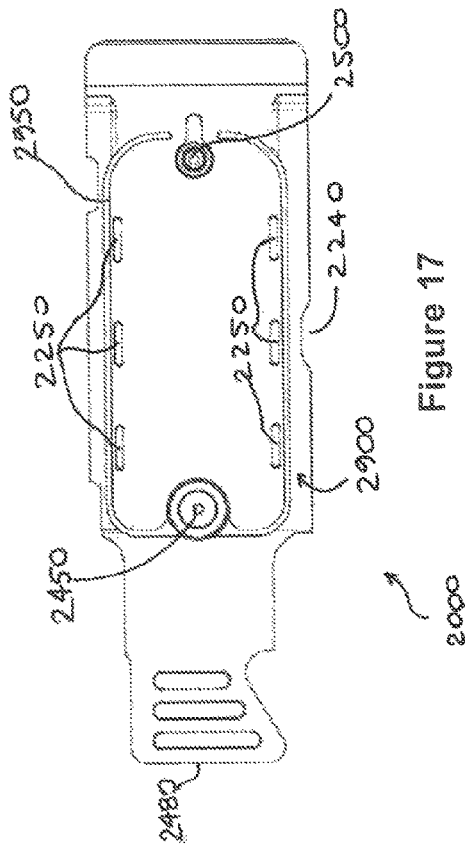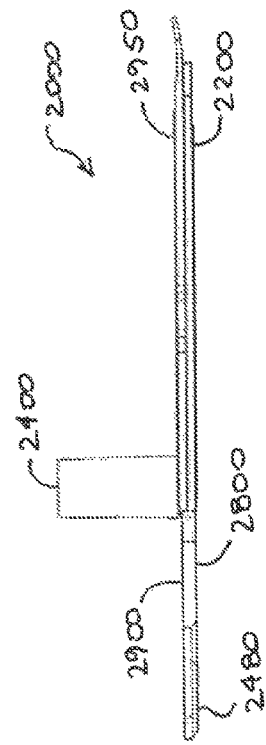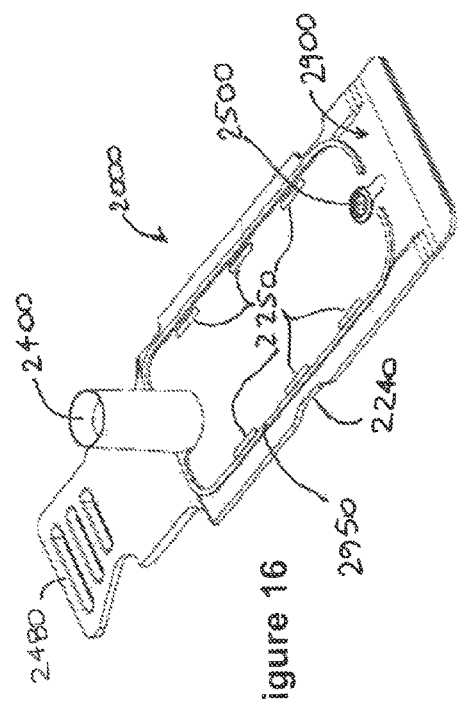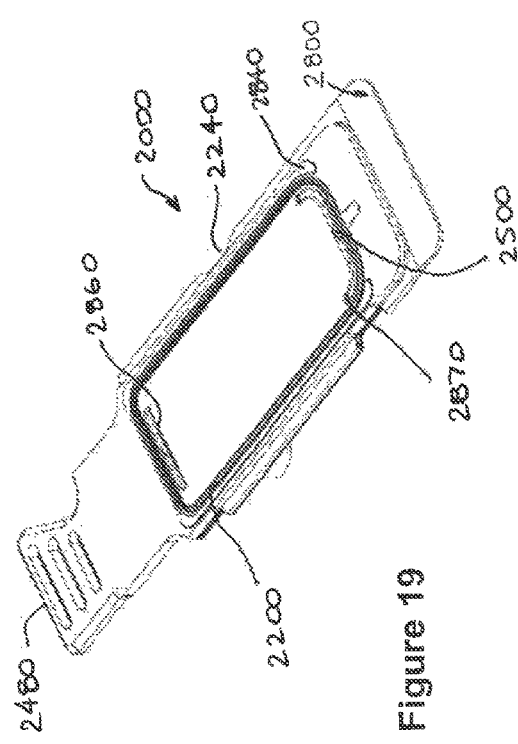

SLIDE STAINING ASSEMBLY AND COVER MEMBER

CROSS REFERENCE TO RELATED APPLICATIONS

This application is a National Stage of International Application No. PCT/AU2013/001267, filed on Nov. 1, 2013, which claims priority from U.S. Provisional Application No. 61/721,280, filed on Nov. 1, 2012, the contents of all of which are incorporated herein by reference in their entirety.

FIELD OF THE INVENTION

The present invention relates to a slide staining assembly, typically for use in a laboratory instrument, to facilitate automated staining of samples on slides. It relates particularly but not exclusively to an assembly configured to releasably retain a cover member for forming a reaction chamber with a slide, and to a cover member per se.

BACKGROUND TO THE INVENTION

Immunohistochemical staining and in situ nucleic acid analysis are tools used in histological diagnosis and the study of tissue morphology. Immunohistochemical staining relies on the specific binding affinity of antibodies with epitopes in tissue samples, and the increasing availability of antibodies which bind specifically with unique epitopes present only in certain types of diseased cellular tissue. Immunohistochemical staining involves a series of treatment steps conducted on a tissue sample (typically a section) mounted on a glass slide to highlight, by selective staining, certain morphological indicators of disease states.

Typical treatment steps include pretreatment of the tissue sample to reduce non-specific binding, antibody treatment and incubation, enzyme labelled secondary antibody treatment and incubation, substrate reaction with the enzyme to produce a fluorophore or chromophore highlighting areas of the tissue sample having epitopes binding with the antibody, counterstaining, and the like. Between each treatment step, the tissue sample must be rinsed to remove unreacted residual reagent from the prior step. Most treatment steps involve a period of incubation typically conducted at ambient temperature of around 25° C. up to around 40° C., while cell conditioning steps are typically conducted at somewhat higher temperatures, e.g. 90° C. to 100° C. In-situ DNA analysis relies upon the specific binding affinity of probes (DNA binding proteins) with unique nucleotide sequences in cell or tissue samples and similarly involves a series of process steps, with a variety of reagents and process temperature requirements. Some specific reactions involve temperatures up to 120° C. to 130° C.

Instrumentation and automated sample processing systems exist for automating some steps in the treatment processes discussed above. However, current systems that involve the use of reaction chambers often result in drying out of tissue samples in between the application of reagents. To compensate, there is a need to constantly hydrate the tissue samples. Automated application of hydration solution to the tissue samples requires use of the robotic reagent dispensation system of the instrument. Because of sample dehydration in automated systems, it is necessary to add extra treatment steps to the process which limits the availability of robotic dispensers for substantive steps required for other reactions being undertaken on the instrument.

Some systems have been designed to reduce sample dehydration by employing a somewhat closed reaction chamber over the slide, into which reagents are introduced. Many of these systems rely on wicking action to draw reagents over the tissue sample. These systems require precise, accurate application of the reagent to a wicking target to ensure consistent and even flow of the reagent into the reaction chamber. If the system loses calibration, application of reagents can miss the wicking target. The adverse effects can be significant and give rise to sample deterioration, wastage of reagent, poor staining, loss of instrument time and delays in sample processing which can have serious implications for patients. To avoid such issues, regular instrument calibration by qualified technicians is required to ensure accurate reagent application, consistent reagent flow and therefore consistent sample staining.

The present invention is aimed at improving upon existing sample staining systems, and/or overcoming or alleviating some of the problems of the prior art.

The discussion of the background to the invention included herein including reference to documents, acts, materials, devices, articles and the like is intended to explain the context of the present invention. This is not to be taken as an admission or a suggestion that any of the material referred to was published, known or part of the common general knowledge as at the priority date of any of the provisional claims.

SUMMARY OF THE INVENTION

Viewed from one aspect, the present invention provides a sample processing assembly for treatment of a sample on a substrate, the assembly including: mounting surface for the substrate; and a closure body configured to releasably retain a cover member, the closure body being movable between an open position and a substantially closed position. When a substrate is placed in the assembly and the closure body is in the substantially closed position while retaining a cover member, a reaction chamber is formed for processing a sample.

In a preferred embodiment, the assembly includes at least one first guide configured to limit movement of a substrate, such as a pathology slide, in at least a first direction during placement of the substrate in the assembly. Ideally, the at least one first guide is a protrusion on the mounting surface although it may take other forms. Preferably, there is also provided at least one second guide on the mounting surface. A second guide limits movement of the substrate in a second direction which is different from the first direction. Typically the first and second directions are arranged orthogonally. Ideally, the at least one second guide is a protrusion which is shaped to cooperate with a corresponding notch in a cover member. In use, the at least one second guide and corresponding notch in the cover member cooperate for optimal alignment of the cover member for forming a reaction chamber with a substrate surface. The reaction chamber may be formed by a substrate/slide on a mounting surface, or a mounting surface without the slide in place. In the former arrangement, the reaction chamber facilitates controlled treatment of a sample on a slide with reagents dispensed into the reaction chamber. In the latter, the reaction chamber facilitates washing of the cover member with wash reagents dispensed into the chamber.

Preferably, the assembly includes closing biasing means for applying a biasing force such that the closure body is biased in the substantially closed position. An opening biasing means may also be provided, for applying an opening biasing force. Preferably, the closing biasing means is configured to apply a larger biasing force than the opening biasing means.

In some embodiments, the assembly includes a detention arm with a detent that is arranged to cooperate with a recess in the closure body to detain the closure body in the closed position. In such arrangement, a bearing surface is disposed toward one end of the detention arm, such that when an opening force is applied to the bearing surface, the detent is released from the recess in the closure body and the closure body moves to the open position.

A removable housing may be provided on the closure body to conceal operational components located therein. Ideally, the removable housing includes a contour, hood or clip configured to orientate tubing within the closure.

A force distribution member may be provided for distributing the force applied to the closure body so that it is substantially evenly applied, to achieve a substantially even seal around the reaction chamber. A thermo module may also be coupled with the mounting surface of the assembly. The thermo module is operable to vary the temperature within the reaction chamber to accelerate or influence treatment steps. Ideally, the thermo module is under the control of a controller built into an instrument incorporating the assembly. The controller may also control opening and closing of the assembly, placement of a substrate therein, dispensing of reagents, application of positive and negative pressures, and the like.

In a preferred embodiment, the closure body includes a first fluid flow path configured for fluid communication with a fluid port in a cover member when retained by the closure body. The first flow path permits fluid transfer between the reaction chamber and a fluid source associated with the sample processing assembly when the assembly is in use.

Ideally, coupling means are provided for releasably attaching a cover member to the closure body. The coupling means may include one or more projections on one of the closure body and the cover member for engaging a surface on the other of the closure body and the cover member forming a releasable coupling there between. One of the closure body and the cover member may also include a release tab for releasing the coupling, thereby enabling release of the cover member from the closure body. Alternatively, the coupling means may include a track or guide channel or other means for slidingly coupling the cover member and the closure body.

In some embodiments, the mounting surface of the assembly includes one or more recesses. Ideally, these are arranged co-linearly with at least part of an interior wall of a cover member when retained by the closure body in a substantially closed position. The positioning of these recesses facilitates cleaning of reagent from at least part of the cover member wall during use of the assembly in a cover member wash phase. The mounting surface may also include an opening couplable with a second fluid flow path facilitating fluid transfer between the opening and a fluid source. The second fluid flow path may be used to hold a substrate on the mounting surface, e.g. during opening of the assembly after use, by application of a vacuum through the mounting surface opening to the underside of the substrate. It may also be used to deliver or withdraw wash reagent from a chamber formed between the mounting surface and the cover member after a cover member wash phase.

Viewed from another aspect, the present invention provides a cover member for use in a sample processing assembly such as the kind referred to above. The cover member has a first side; a second side opposing the first side; a void on a first side, the void forming a reaction chamber when the cover member contacts a substrate; a first fluid flow port for receiving reagent into the reaction chamber; and at least one notch. The cover member is configured for releasable engagement with a closure body of the sample processing assembly and the at least one notch is shaped to cooperate with a corresponding protrusion on one of a mounting surface of the sample processing assembly and the closure body of the sample processing assembly, such that when in use, the notch and protrusion guide the cover member into position in the assembly to form a reaction chamber with a substrate.

Viewed from another aspect still, the present invention provides a cover member for use in a sample processing assembly, the cover member having a first side, a second side opposing the first side, a void on a first side, the void forming a reaction chamber when the cover member contacts a substrate; and a compressible member on the first side configured to form a seal around the reaction chamber when in use, the compressible member material further extending around a fluid flow port in the cover member and forming a sealing annulus around an opening of fluid flow port on the cover member second side. The cover member is configured for releasable engagement with a closure body of the sample processing assembly. In one embodiment, the void is defined by the compressible member. In another embodiment, the void is defined, at least in part, by a void portion or cavity in the cover member first side.

The substrate with which the cover member forms a reaction chamber may be a slide, such as a histology slide (e.g. for sample treatment steps), or a mounting surface of the assembly (e.g. for a cover member wash phase). Ideally, there are two or more notches.

It is preferred that the cover member is manufactured, at least in part, from a compliant material. The cover member may be manufactured or coated at least in part from a material selected from the group including: Polycarbonate, Polyoxymethylene (acetal), Polyether ether ketone (PEEK), polyethylenes including high density polyethylene (HDPE) and ultra-high molecular weight polyethylene (UHMW-PE), Teflons including Teflon PE and Polypropylenes including Fluorinated ethylene propylene (FEP), and Cyclic Olefin Copolymers (COC).

In some embodiments the cover member includes at least one biasing arm. The biasing arm is configured such that when in use in a sample processing assembly, the biasing arm abuts a reference member on the closure body and, during final closure of the closure body, urges the cover member toward a protrusion on the assembly. Ideally, there are two biasing arms urging the cover member, during the final stages of closing, toward to protrusions on the mounting surface which cooperate with two corresponding notches in the cover member, for optimal alignment of the cover member in the assembly prior to use.

Preferably the cover member includes coupling means for releasably coupling the cover member with a closure body of the sample processing apparatus. A tab for releasing the coupling means may also be provided. In a preferred embodiment, the coupling means is adapted for slidable coupling of the cover member and the closure body.

In one or more embodiments, the cover member includes a release member on the first side. The release member may take the form of a tongue or sprung release member configured to aid separation of the cover member from a substrate by overcoming any forces of surface tension or stiction which could otherwise lift the substrate from the mounting surface when the assembly is opened after a treatment phase. In other arrangements, the release member may be provided on the closure body with which the cover member is used.

In an embodiment, the cover member includes a reservoir configured to receive and store a quantity of fluid sufficient for a plurality of treatment steps. A fluid inlet port is also provided for fluid ingress from the reservoir into the reaction chamber. The reservoir is in communication with the fluid inlet port and may include one or more inclined internal walls configured to direct fluid into the first fluid port. In some embodiments, thicker wall portions are located more distally of the void than thinner wall portions to minimise the negative influence of manufacturing tolerances on the size and consistent shape of the void which forms the reaction chamber.

Ideally, a fluid flow port is provided for fluid communication between the reaction chamber formed by the void and/or sealing member and a fluid source couplable with the fluid flow port, e.g. through a corresponding opening in a closure body retaining the cover member. Preferably, the fluid flow port has an opening on the second side of the cover member. This opening may be substantially surrounded by a compliant material configured such that when in use, a substantially sealing coupling is formed with the corresponding opening in the closure body. The compliant material may be provided as part of a unitary piece of compressible material extending around the fluid flow port and further forming a compressible member which performs as a sealing gasket around the reaction chamber when in use.

In some embodiments, one or more slots are provided in the cover member first side and are arranged to receive, during manufacturing of the cover member, compressible member material, configured to form a sealing gasket around the reaction chamber when in use. Preferably, one or more of the slots are wedge shaped with the widest part of the wedge-shaped opening oriented toward the cover member second side. One or more slots may be through holes extending all the way through the cover member from the first side to the second side. In an embodiment, an end stop feature is provided on the cover member first side to limit compression of the compressible member during use. In some embodiments, a spacing member is provided on the cover member second side, the spacing member adapted to contact a bearing surface of a closure body with which the cover member is used.

In some embodiments, the cover member includes one or more cavities or fluid control features in the cover member first side. In one embodiment, a first cavity in the cover member first side is in fluid communication with a fluid inlet and is shaped to form a substantially orthogonal fluid front within the reaction chamber when in use. A second cavity in the cover member first side may be provided, in fluid communication with a fluid outlet. The second cavity is located toward a fluid outlet (evacuation) end of the reaction chamber and is shaped to draw fluid from a fluid front within the reaction chamber when in use, for evacuation through the fluid outlet. Ideally, the second cavity is contoured to mitigate fluid and debris collection in corners of the reaction chamber.

In some embodiments, the cover member includes one or more structural features in the form of a ridge or protrusion extending along part or a length of a surface of the cover member. Ideally, the one or more structural features do not affect or diminish the size or flow characteristics of the reaction chamber formed by the cover member when in use. The structural features impart support to substantially preclude warping, bending or twisting of the cover member, e.g. when heated and/or cooled during use of the cover member to perform a sample processing step. In one embodiment, the structural feature is a strengthening ridge or strip running substantially the whole elongate length of the cover member, although other structural features are also contemplated such as orthogonal, parallel, intersecting, angled or otherwise orientated features.

Viewed from another aspect, the present invention provides a sample processing assembly for treatment of a sample on a substrate, the assembly including: a mounting surface for the substrate; a closure body configured to releasably retain a cover member, the closure body being movable between an open position and a substantially closed position; and at least one first guide configured to limit movement of a substrate in at least a first direction during placement of the substrate in the assembly; wherein, when a substrate is placed in the assembly and the closure body is in the substantially closed position when retaining a cover member, a reaction chamber is formed for processing a sample.

Viewed from yet another aspect, the present invention provides a sample processing assembly for treatment of a sample on a substrate, the assembly including: a mounting surface for the substrate; a closure body configured to releasably retain a cover member, the closure body being movable between an open position and a substantially closed position; and biasing means for applying a biasing force such that the closure body is biased in the substantially closed position; wherein, when a substrate is placed in the assembly and the closure body is in the substantially closed position when retaining a cover member, a reaction chamber is formed for processing a sample.

Viewed from another aspect still, the present invention provides a cover member for use in a sample processing assembly, the cover member having: a first side; a second side opposing the first side; a void on a first side, the void forming a reaction chamber when the cover member contacts a substrate; a first fluid flow port for receiving reagent into the reaction chamber; and releasable engagement means for slidably coupling the cover member with a closure body of the sample processing assembly.

The present invention also provides a new approach to manufacturing cover members, particularly cover members according to the invention which incorporate a compressible member. Such a method includes forming a cover member body by injection moulding or the like, and injecting a flowable compressible material into a mould containing the cover member body, the mould configured to form the compressible member on the cover member first side when the flowable compressible material sets. Using this technique, the flowable compressible material fills one or more slots and contours in the cover member first side to form the compressible member. The fluid compressible material may also form a via around a fluid flow port in the cover member terminating in a sealing annulus around the fluid flow port on the cover member second side, the sealing annulus comprising part of a unitary material piece with the compressible member on the cover member first side.

BRIEF DESCRIPTION OF THE DRAWINGS

The present invention will now be described in greater detail with reference to the accompanying drawings. It is to be understood that the embodiments shown are examples only and are not to be taken as limiting the scope of the invention as defined in the claims appended hereto.

FIG. 16 is an isometric top view of a cover member according to an embodiment of the invention.

FIG. 17 is a top plan view of the cover member of FIG. 16.

FIG. 18 is a side view of the cover member of FIGS. 16 and 17.

FIG. 19 is an isometric bottom view of the cover member of FIGS. 16 and 17.

DETAILED DESCRIPTION

Figure 1:
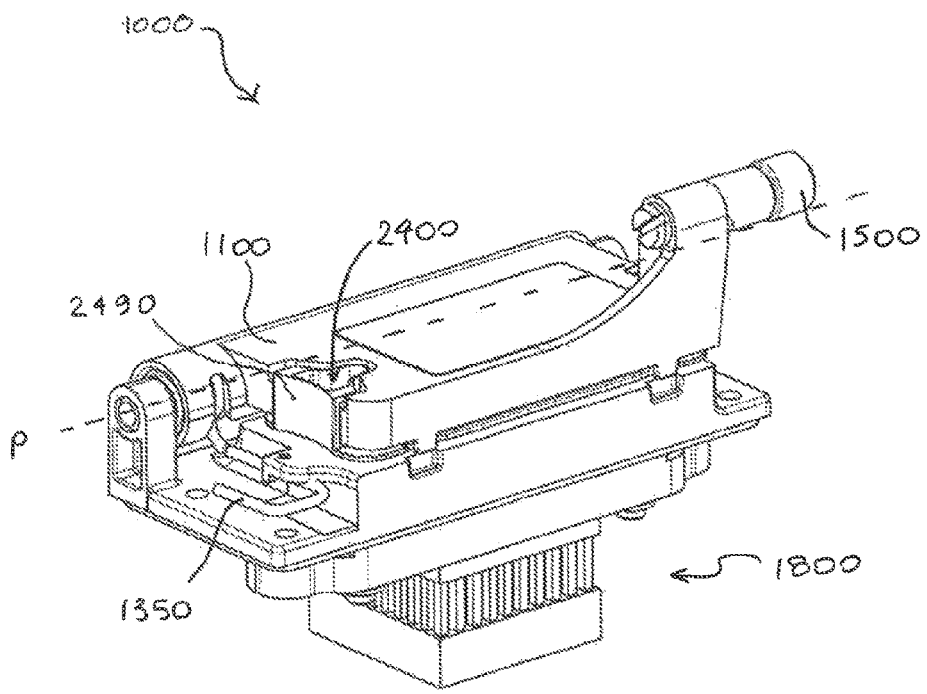
FIG. 1 is an isometric view of a sample processing assembly in a substantially closed position when viewed from the front, according to an embodiment of the invention.
Figure 11:
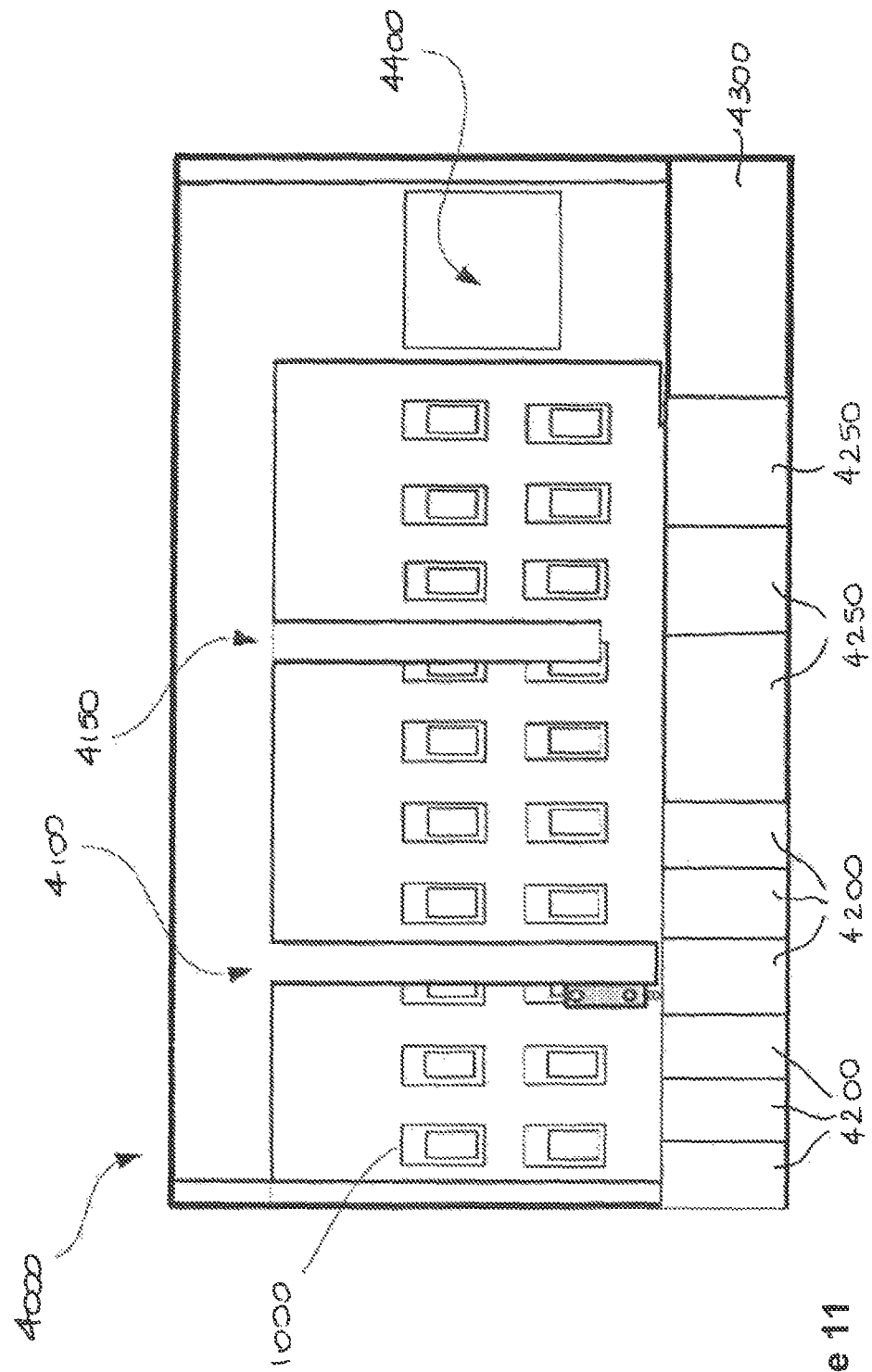
FIG. 11 is a schematic illustration of an instrument with which a sample processing assembly and cover member according to the present invention may be used.

FIG. 1 is a schematic illustration of a sample processing assembly 1000 according to an embodiment of the invention. The assembly may be provided as part of an instrument 4000 illustrated in FIG. 11, which has a robotic head 4100 which opens and closes the assembly closure body, and dispenses reagent through a probe on the robotic head into the assembly in accordance with instructions received from a controller 4400 forming part of the instrument. Ideally, the instrument contains a plurality of sample processing assemblies 1000 of the kind described and claimed herein, such that a number of individual samples may be processed by the instrument 4000 in an automated fashion with little or no manual intervention. Such an instrument may employ a single robotic head 4100 for dispensing reagents, or a second or subsequent robot 4150 may be involved.

Typically, the instrument 4000 houses containers of reagent 4200, 4250, typically fluid reagent, of the various types that are required to complete the processing steps controlled by the controller 4400. A robotic dispensing head 4100, 4150 is coupled to the containers 4200, 4250 by a fluid distribution system (tubing between the containers and the head) and dispenses fluid into a sample processing assembly 1000 using a probe. Fluid may also be dispensed from reagent containers 4200, 4250 on board the instrument 4000 via the fluid distribution system absent the probe, i.e. using tubing. A probe and robotic dispensing system are described in U.S. provisional patent application 61/721,269 entitled "A Fluid Transport System" having a filing date of 1 Nov. 2012; and U.S. provisional patent application 61/721,257 entitled "A Slide Transport System" having a filing date of 1 Nov. 2012, the entire contents of both of which are hereby incorporated herein by reference. There is also a waste system with waste reservoir 4300 for disposing waste reagent that may be collected from a sample processing assembly 1000 and/or various wash stations in the instrument. The instrument may recycle some reagents, or may collect some reagents for recycling or disposal off-board the instrument.

Figure 2:
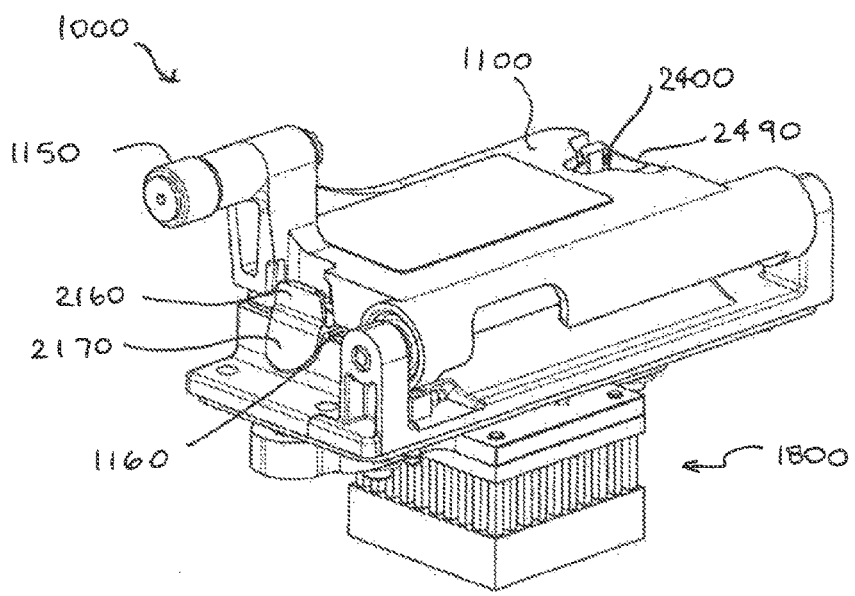
FIG. 2 is an isometric view of the sample processing assembly of FIG. 1 when viewed from the rear.

FIG. 1 shows the assembly 1000 in a substantially closed position and viewed from the front. FIG. 2 shows the assembly viewed from the rear. Both views clearly show closure body 1100. A cover member 2000 (FIGS. 7, 8) is retained by the closure body 1100 and reservoir 2400 of the cover member is visible in both Figures. Cover member thumb grip 2490 is shown in FIG. 1 while FIG. 2 shows coupling projection 2160 and release tab 2170 of the cover member 2000 according to one embodiment.

Figure 3:
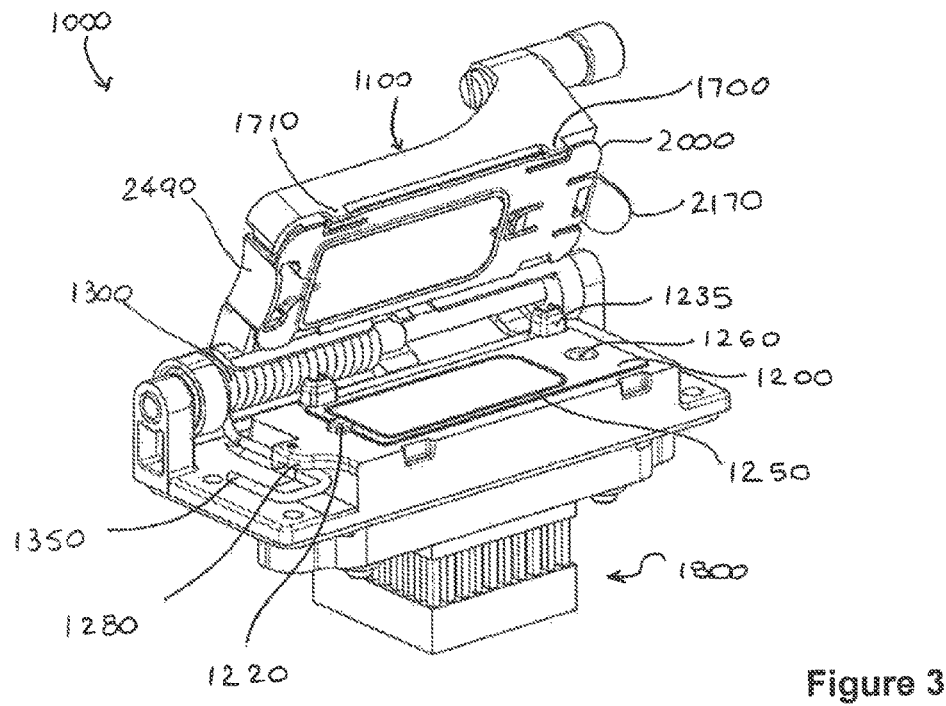
FIG. 3 is an isometric view of the sample processing assembly of FIG. 1 viewed from the front when in an open position with the closing biasing means engaged and a cover member retained in the closure body.
Figure 9:
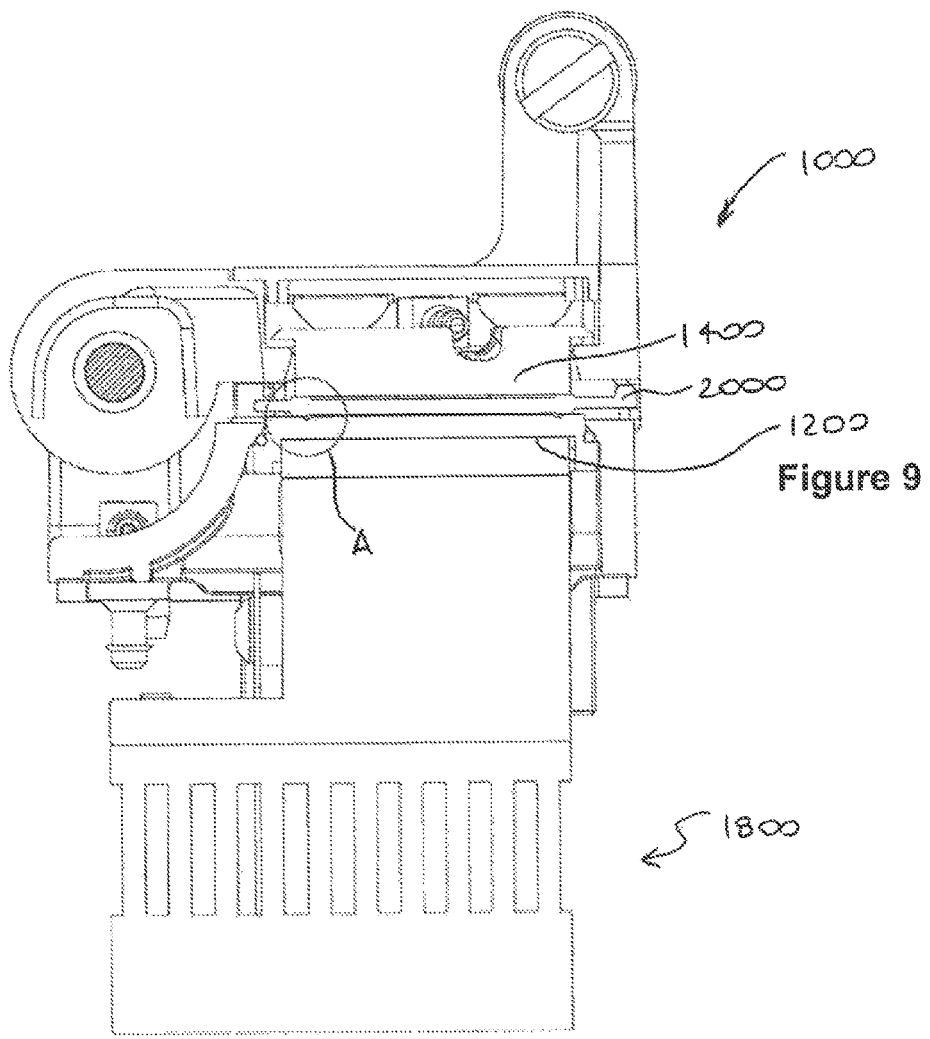
FIG. 9 is a side view of the sample processing assembly of FIG. 1 with enlarged portion A shown in FIG. 9A.

FIG. 3 is a schematic illustration of the sample processing assembly of FIG. 1 viewed from the front when in an open position. Mounting surface 1200 is provided to support a substrate, not shown, such as a slide onto which a sample has been mounted for processing using the assembly 1000. Closure body 1100 is configured to releasably retain a cover member 2000 as shown. The closure body 1100 is movable, relative to mounting surface 1200, between an open position (FIGS. 3, 4) and a substantially closed position (FIGS. 1, 2, 9).

Figure 4:
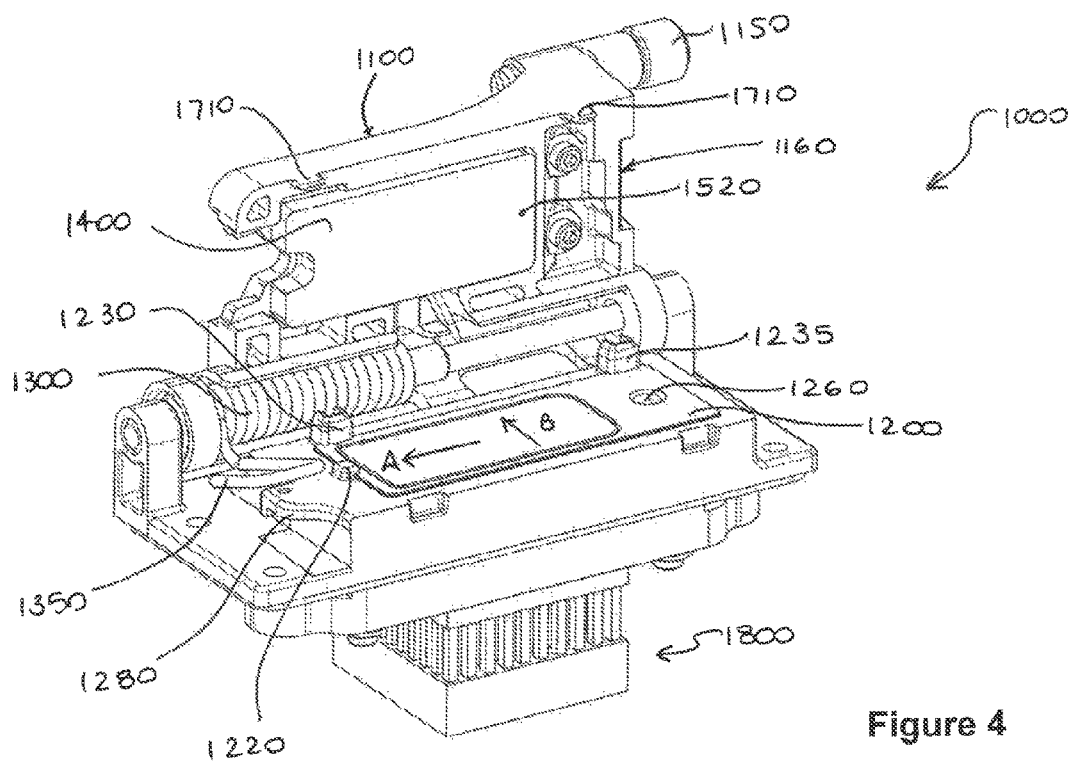
FIG. 4 is an isometric view of the sample processing assembly of FIG. 3 with the closing biasing means disengaged and cover member removed.

Ideally, the sample processing assembly 1000 has a bearing surface 1150 on closure body 1100 that may be contacted by part of the robotic head 4100 to actively open the closure body which is normally biased closed. Typically, the bearing surface 1150 includes a cam roller which protrudes from the closure body 1100 and is contacted by a contact member of the robotic head 4100. Thus, as the robotic head 4100 contacts the bearing surface 1150 and moves in direction B (FIG. 4), the closure body 1100 pivots open around axis P (FIG. 1), to an open configuration as shown in FIGS. 3 and 4. It is to be understood however that the direction of opening need not involve pivoting or pivoting alone; separation of the closure body 1100 from the mounting surface 1200 by lifting the closure body or lowering the mounting surface is also contemplated, as well as relative sliding of the two parts to accommodate placement therebetween of a slide/substrate carrying a sample for processing.

Ideally, the substrate is placed in the open sample processing assembly using the robotic head 4100, which conveys a substrate with sample into the assembly 1000 in an automated fashion, under the control of a controller 4400. Such a system is described in U.S. provisional patent application 61/721,257 referred to above. This may involve the robotic head 4100 controlling movement of the substrate e.g. by sliding on mounting surface 1200 and into position, ready for closure body 1100 to be closed. The robotic head 4100 may manipulate the substrate using e.g. grippers, a vacuum or any other suitable means to hold/grasp the substrate for placement within the assembly 1000.

To assist with positioning, at least one first guide 1220 is provided in the form of a protrusion or post on the mounting surface 1200 to limit movement of the substrate in at least a first direction A (FIG. 4). Thus, when the substrate is placed using robotic head 4100, it slides across mounting surface 1200 until it reaches first guide 1220 which provides a datum point limiting further movement. One or more further first guides may be provided to limit direction of the substrate in direction A, if necessary.

In a preferred embodiment, one or more second guides 1230, 1235 are also provided, typically in the form of protrusions or posts on the mounting surface 1200, to limit movement of the substrate in a direction B (FIG. 4). It is to be understood that the substrate may be moved in direction A and direction B in any order, and positioning may be iterative such that the substrate moves in directions A-B-A or B-A-B etc. The second guides provide further datum points to optimise placement of the substrate within the sample processing assembly. In an embodiment, the one or more second guides 1230, 1235 are shaped to cooperate with corresponding notches 2230, 2235 in a cover member 2000 when retained in the closure body 1100. In this arrangement, the at least one second guide 1230, 1235 and corresponding notches 2230, 2235, cooperate during closing of the closure body 1100 for optimal alignment of the cover member 2000 over the substrate (not shown) to form a reaction chamber.

The reaction chamber thus formed between the substrate and the cover member 2000 when the assembly 1000 is in a substantially closed position protects tissue samples on the substrate surface by minimising exposure to air; a drawback which has led to drying out of samples in the past. In some prior art instruments sample drying has necessitated regular rehydration during processing. This step may be avoided by use of embodiments of the present invention.

Figure 10:
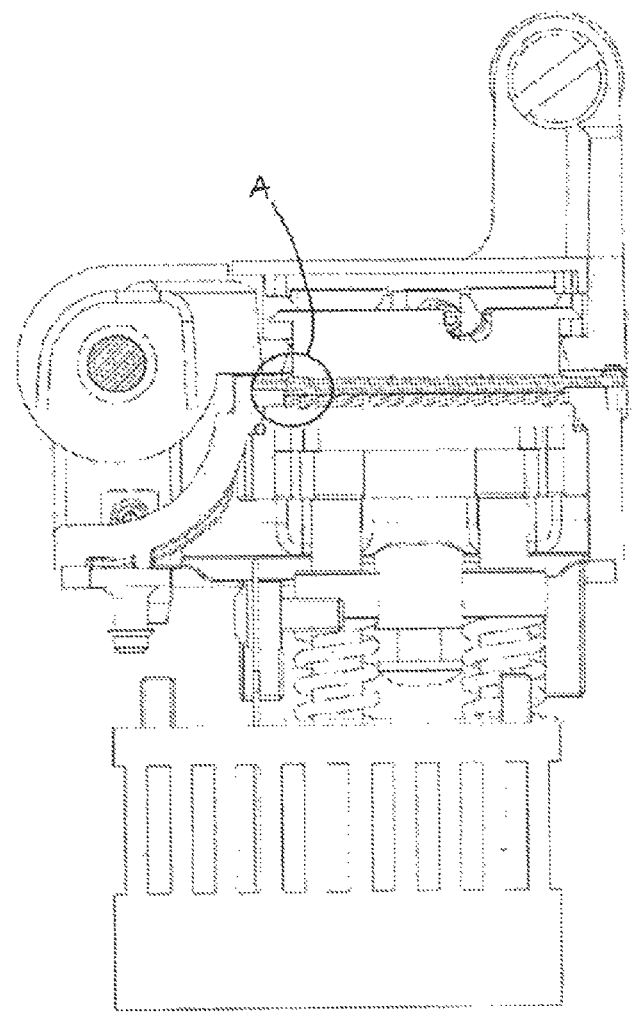
FIG. 10 is a side sectional view of the sample processing assembly of FIG. 1 with a slide positioned therein, with enlarged portion A shown in FIG. 10A.
Figure 10A:
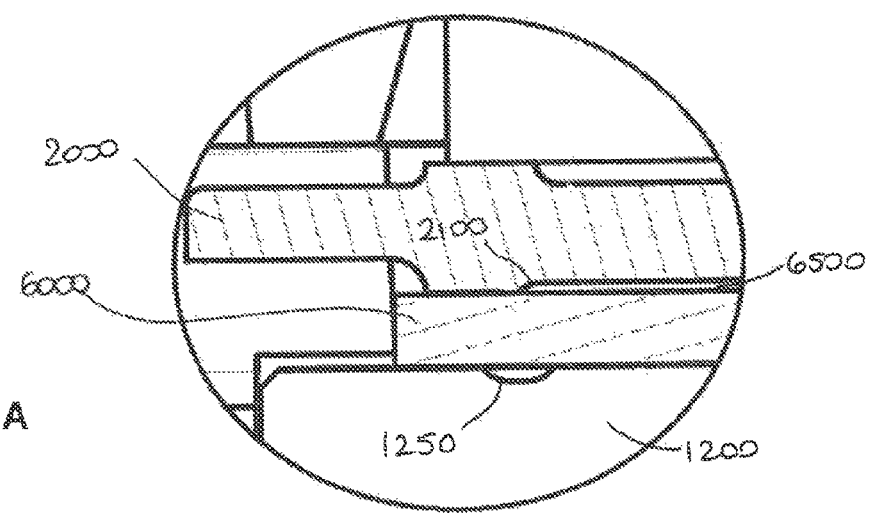

FIG. 3 shows biasing means 1300, which biases closure body 1100 toward a substantially closed position by pressing on a force distribution member 1400 which is coupled to or integral with the closure body when spring clip 1350 is engaged with lip 1280 on mounting surface 1200. Ideally, force distribution member 1400 is coupled with closure body 1100 in a manner which permits a degree of "floating" in a plane orthogonal to the substrate. This enables the force distribution member 1400 to compensate for small variations in substrate thickness (as may arise between slide manufacturers) when the closure body 1100 with cover member 2000 is closed over a substrate. Floating force distribution member 1400 assists in addressing surface variations in substrate surface or cover member surface such as bowing, undulations or other such variations by enhancing flattening of surface variations. Force distribution member 1400 also compensates for absence of a substrate during a wash phase. FIG. 10 is a side sectional view of the sample processing assembly 1000 with a substrate 6000 positioned therein. Enlarged portion A shown in FIG. 10A shows in greater detail substrate 6000 positioned on mounting surface 1200. Cover member 2000 is retained by closure body 1100 and together with substrate 6000, defines a reaction chamber 6500.

The spring clip 1350 may be released as in FIG. 4 to decouple the closing biasing means 1300 from the lip 1280 so that the closure body 1100 may be fully opened, e.g. for easier access during servicing. The force applied by biasing means 1300 when engaged may be provided through force distribution member 1400 at a single point, or it may be provided at a plurality of locations. The force distribution member 1400 may comprise an undulating surface, raised portions, corrugations or other raised points distributed across all or a portion of the substrate facing surface. In an embodiment, the force distribution member 1400 may comprise an undulating surface, raised portions, corrugations or other raised points distributed across all or a portion of at least two surfaces. Ideally, force distribution member 1400 distributes the closing biasing force applied to the closure body 1100 somewhat evenly so that when in the substantially closed position, a seal forms at the junction between the cover member 2000 and a substrate when located in the assembly 1000 to form a reaction chamber 6500 between the two. The magnitude of force applied by the biasing means 1300 is sufficient to form this seal whilst also able to be overcome by the robotic head 4100 when opening the assembly by applying an opening force to bearing surface 1150.

Figure 12:
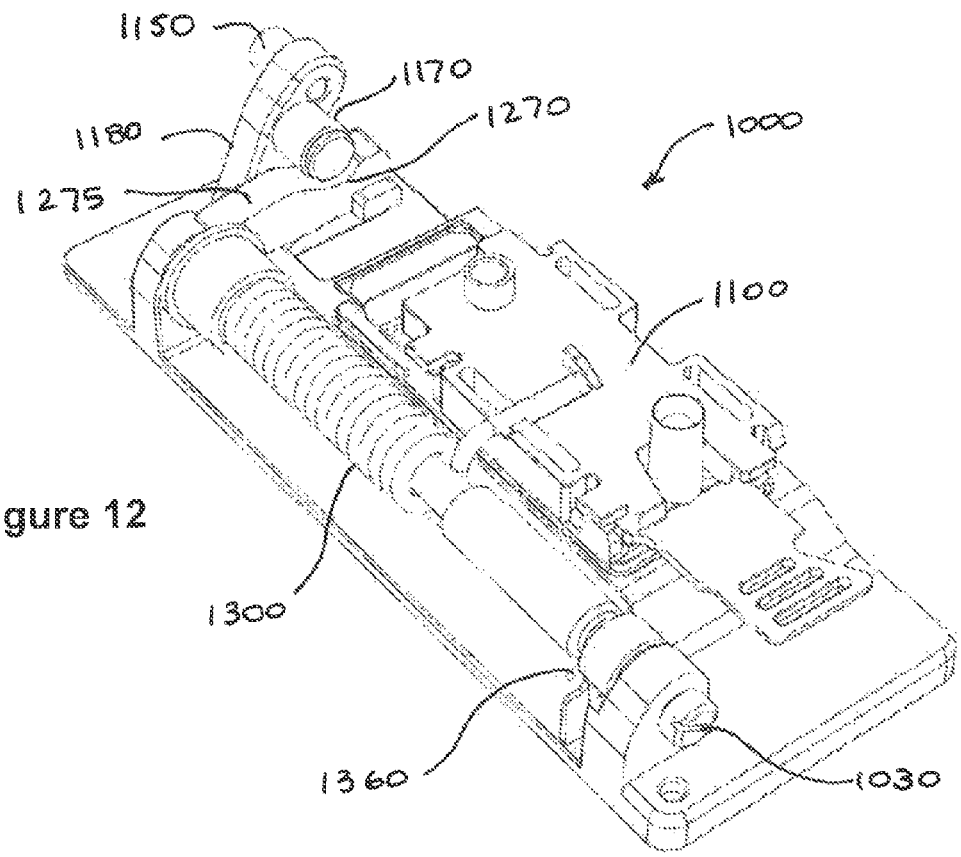
FIG. 12 is an isometric view of a sample processing assembly according to an embodiment of the invention in the closed position.
Figure 13:
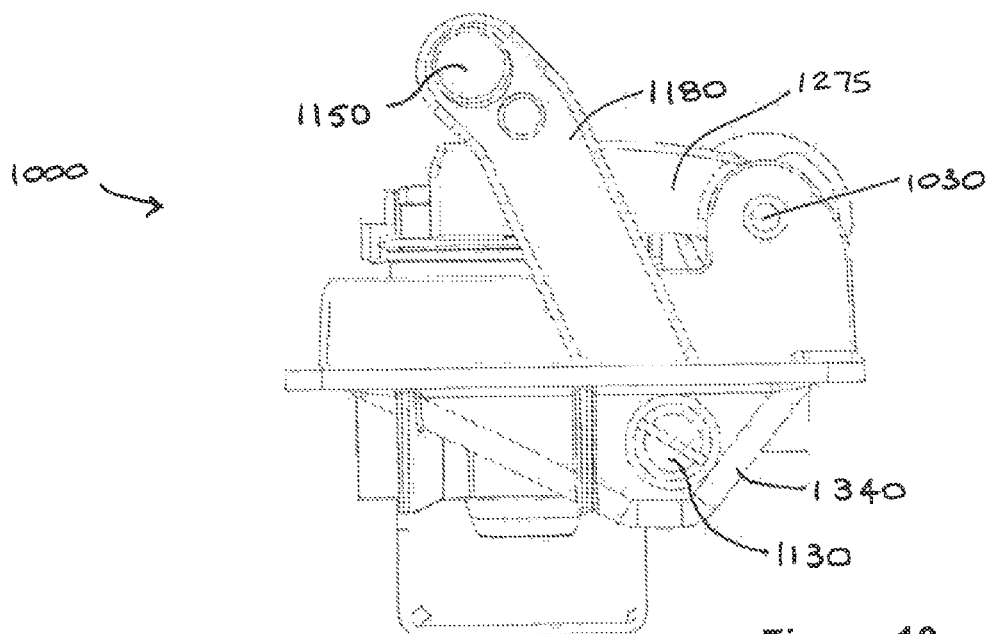
FIG. 13 is an end view of the sample processing assembly of FIG. 12.

FIGS. 12 and 13 show a further embodiment of the sample processing assembly 1000 where the closure body 1100 is detained in the closed position with a detent 1170 protruding from a detention arm 1180 that is arranged to cooperate with a recess 1270 in a recess arm 1275 on the closure body 1100 when in the closed position. In the embodiment shown in FIG. 12, the slide treatment module 1000 includes two opposing biasing means. Specifically, an opening biasing means 1360 is provided for applying a biasing force to the closure body 1100 to pivot the closure body 1100 to the open position; a larger, closing biasing means 1300 is provided for applying a biasing force to the closure body 1100 to pivot the closure body to the closed position. In the embodiment illustrated, the biasing means are springs. In some embodiments, the opening biasing means 1360 applies a force of approximately 5 to 10 N and the closing biasing means 1300 applies a closing force of approximately 45 N. By operation of the detent 1170 which normally sits in recess 1270, closure body 1100 can be detained in the closed position against the action of an opening force arising from opening biasing means 1360, or it can be detained to prevent accidental opening of the closure body 1100 of the slide treatment module 1000.

In the embodiments illustrated in FIGS. 12 and 13, bearing surface 1150 is disposed at one end of detention arm 1180 so that robotic head 4100 contacts the bearing surface 1150 to move the closure body 1100 to the open position. Thus, when robotic head 4100 contacts bearing surface 1150 to apply an opening force, detent 1170 is released from recess 1270 enabling the closure body 1100 to pivot to the open position about pivot 1030 disposed on slide treatment assembly 1000.

Figure 14:
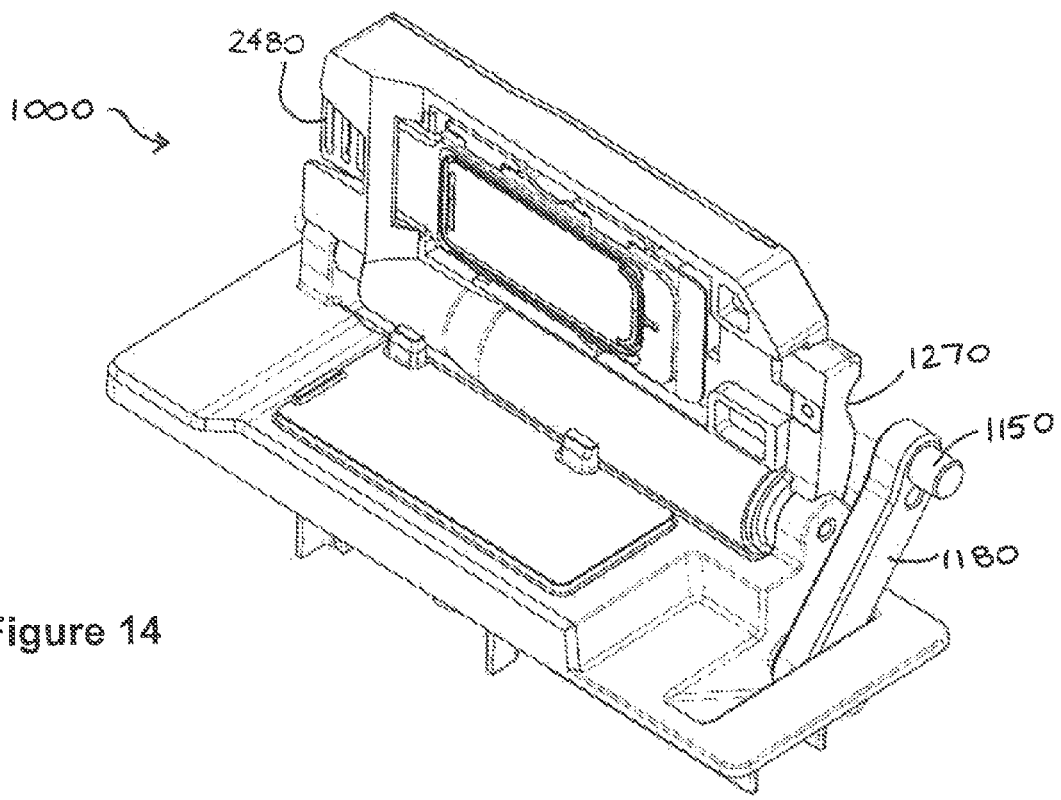
FIG. 14 is an isometric view of the sample processing assembly of FIGS. 12 and 13 in an open condition.

FIGS. 13 and 14 show the detention arm 1180 in further detail. The detention arm 1180 includes detention pivot 1130 at an opposing end to bearing surface 1150 that is retained by a section of the slide treatment assembly 1000. The detention arm 1180 rotates about detention pivot 1130 as it is moved by the robotic head 4100 between the open and closed positions of the closure body 1100. FIG. 13 shows the detention arm 1180 in the closed position with the detent 1170 within the recess 1270 (not shown in the Figure). FIG. 14 shows the detention arm 1180 in the open position with the detent 1170 disengaged from the recess 1270. In use, the opening action of the robotic head 4100 rotates the detention arm 1180 about detention pivot 1130 so that the end with the detent 1170 tracks along recess arm 1275 to its open position and the closure body 1100 consequently moves to the open position to an angle determined by the angle of the endstop 1340. It will be appreciated that, in the open position, detent 1170 is moved away from recess 1270 of the closure body 1100.

Furthermore, it is to be understood that means other than biasing means can be incorporated into assembly 1000 to open and close the closure body 1100 and bias it toward an open or closed position. For example, after the detent 1170 is released, a motor (not shown) may drive the closure body 1100 to the open position until its final position is reached, bound by movement of detention arm 1180. The motor may also drive the closure body 1100 back to the closed position. In one embodiment, the motor is a screw drive motor although other forms of motor drives are contemplated.

Figure 15:
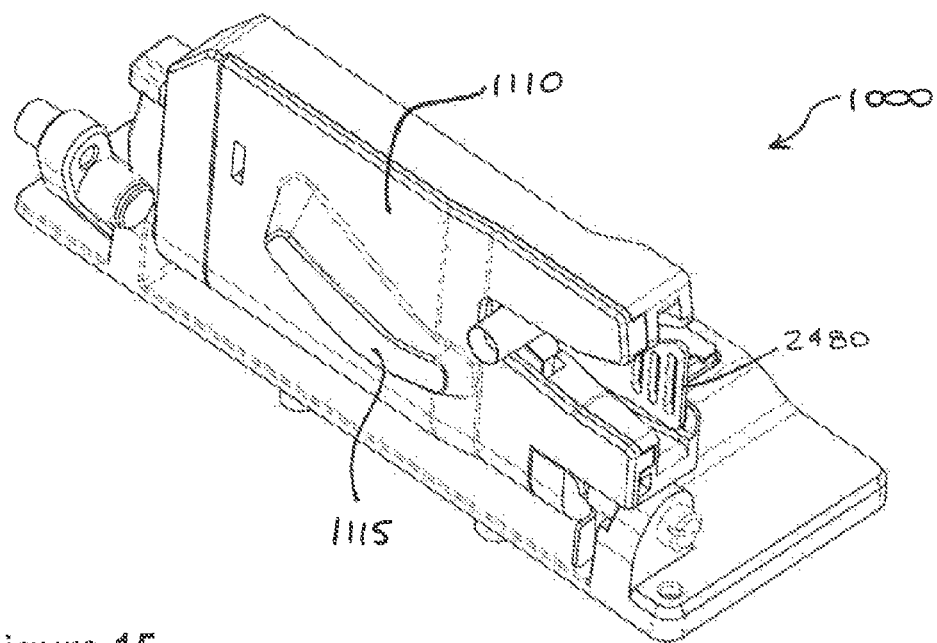
FIG. 15 is an isometric view of a sample processing assembly according to an embodiment of the invention in the open position, with a housing lid concealing internal components of the closure body.

FIG. 15 is an isometric view of a sample processing assembly according to an embodiment of the invention in the open position, with a housing in the form of a removable plastic moulding 1110 concealing internal components of the closure body which are exposed in FIGS. 12 and 13. Plastic moulding 1110 is configured to snap-fit onto the top surface of closure body 1100 to conceal operational components, covering the outlet port 2500, but not the reservoir 2400 (when provided) on cover member 2000 which opens into inlet port 2450. Advantageously, tubing (not shown) which forms part of the fluid path inside cover member 2000 is covered by hood 1115 of the moulding 1110 which controls its orientation within the closure body 1100. This prevents formation of kinks and catching of the tubing on moving parts such as the robotic head 4100. The removable moulding 1110 also provides a neat appearance and is easily removed for cleaning.

Figure 5:
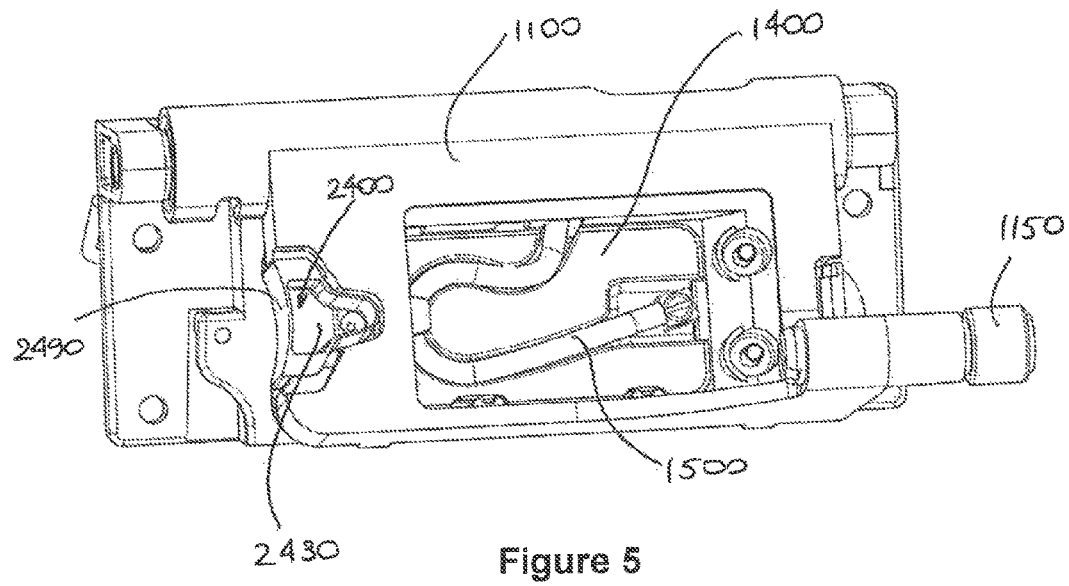
FIG. 5 is a top view of the closure body of FIG. 1 with a housing lid removed revealing internal components.
Figure 6:
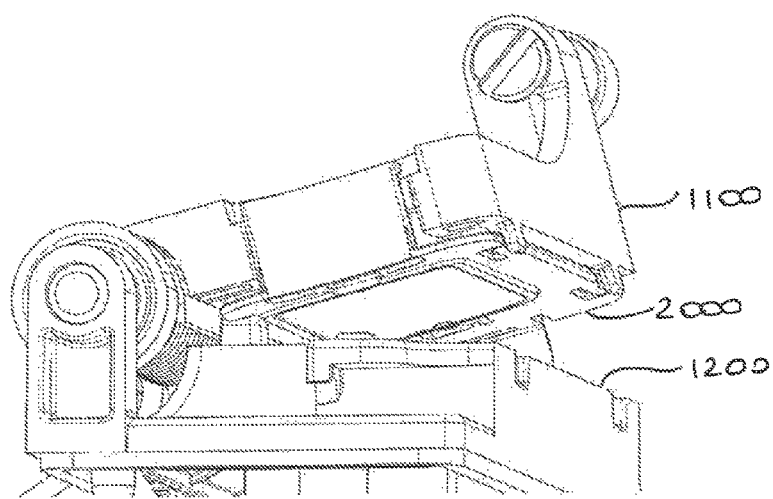
FIG. 6 is an isometric view of the sample processing assembly of FIGS. 1 to 4 with a cover member retained, during closure.

FIGS. 4 and 5 show in greater detail some features of the closure body 1100. A first fluid path 1500 is configured for fluid communication with a fluid management system which is ideally on board the instrument 4000 and under the control of the controller 4400. First fluid path 1500 is also configured for coupling with a fluid flow port 2500 in a cover member 2000 when retained by the closure body 1100, to permit fluid transfer between the reaction chamber and the fluid management system. FIG. 4 shows a fluid opening 1520 in the underside of force distribution member 1400 which, when a cover member is retained by closure body, permits fluid transfer between the first fluid path 1500 and the reaction chamber. Typically, first fluid path 1500 is coupled with a waste fluid line in the instrument which comprises a pressure and/or vacuum or other source configured to apply negative and/or positive fluid pressures to force fluid into or withdraw fluid from the reaction chamber to achieve agitation and/or evacuation of reagent from the reaction chamber. Agitation can assist with bubble management within the reaction chamber during a processing step, increasing the likelihood of reagent contacting a sample on the substrate despite the existence of bubbles in the chamber.

FIG. 5 is a top view of the closure body of FIGS. 1 to 6 with a housing lid removed, revealing internal components including tubing forming the first fluid path 1500 and interior facing surface of force distribution member 1400.

In an embodiment, coupling means in the form of coupling surface 1160 and projections 2160 are provided on the closure body 1100 and cover member 2000 respectively, to releasably retain the cover member within the closure body. Typically, a cover member 2000 is manually coupled with the closure body 1100 to prepare the assembly 1000 for sample processing, although automated coupling and decoupling by the instrument is also contemplated. In the embodiments shown in FIGS. 1 to 10, a user holds the cover member 2000 between the thumb (resting on thumb grip 2490) and index finger (resting at release tab 2170) and click-fits the cover member into the closure body 1100 by applying sufficient pressure for the projection 2160 to flex over and engage with the coupling surface 1160.

Once the cover member 2000 is in place, it may be re-used a number of times before replacement is necessary. To remove for replacement, the user grasps the cover member 2000 between the index finger and thumb, and applies pressure to the release tab 2170 to retract the projection 2160 thereby releasing the cover member 2000 from the closure body 1100. The arrangement of contact surfaces for the thumb and index finger and use of a friction fit coupling facilitate easy exchange of cover members during ongoing service.

In other embodiments, such as those shown in FIGS. 12 to 19, cover member 2000 is slidingly couplable with the closure body 1100. Thus, the cover member 2000 may be located in the closure body 1100 by sliding, where one or more tracks, channels, grooves or rails are provided to align and guide sliding engagement. Spring clips may be provided to avoid accidental removal of the cover member from the closure body. Alternatively, the parts may be friction fit together. Tab 2480 is provided for sliding removal of the cover member 2000 from the closure body. Ideally, tab 2480 has slots, grooves or other textured surface on at least one side to assist with easy gripping by a user. It is to be understood however, that in lieu of the mechanical coupling described herein, other means such as a vacuum, chemical bonding, magnetic, or other mechanical mechanism may be employed to retain a cover member 2000 in position in the closure body 1100.

Figure 7:
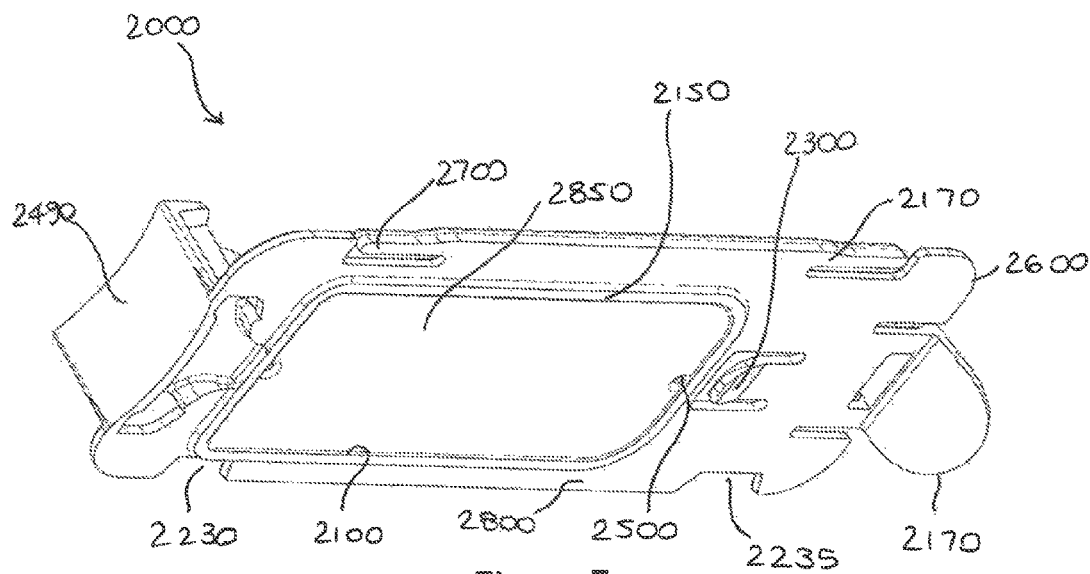
FIG. 7 is an isometric view of a cover member according to an embodiment of the invention, viewed from a first side (bottom).
Figure 8:
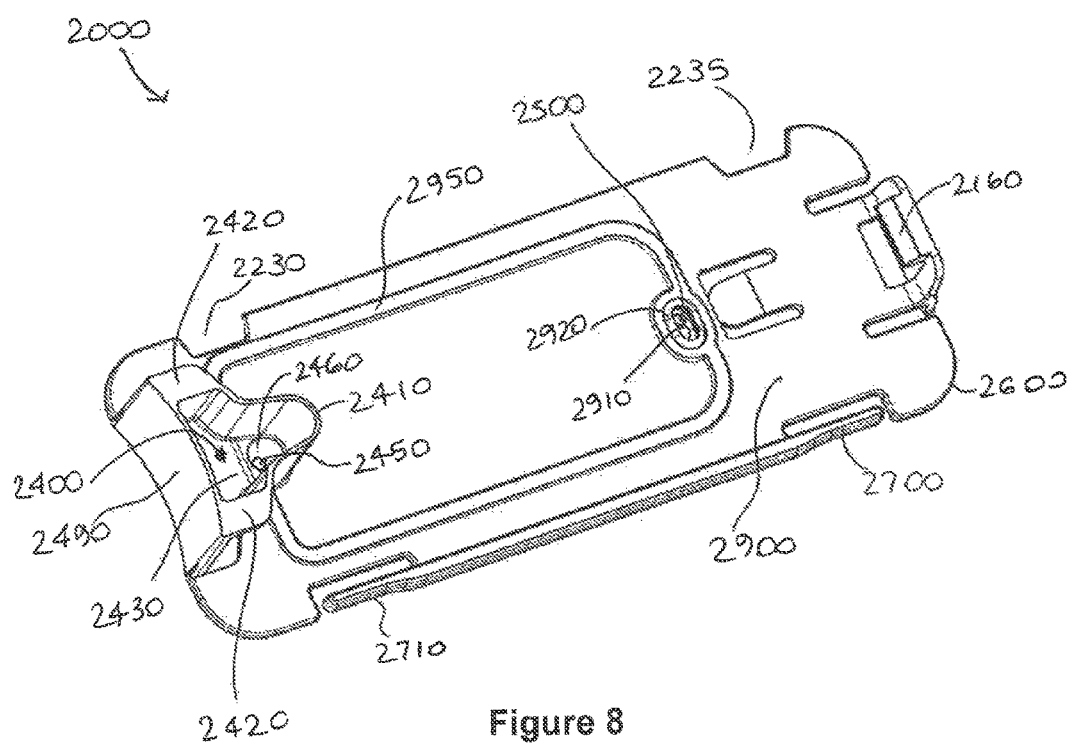
FIG. 8 is an isometric view of the cover member of FIG. 7 viewed from a second side (top).

FIGS. 7 and 8 illustrate an example of a cover member 2000 according to an embodiment of the invention. The cover member has a first side 2800 and a second side 2900 opposing the first side. A void 2850, defined by interior walls 2100 on the first side of the cover member 2000, forms a reaction chamber of 20 µl to 500 µl in volume, more preferably 50 µl to 300 µl and more preferably still, 100 to 200 µl in volume, when the cover member 2000 contacts a substrate in the assembly. Walls 2100 have a thickness which, in use, forms a sealing surface 2150 with a substrate (e.g. in the form of a slide or mounting surface) below. A first fluid flow port 2450 for receiving reagent into the reaction chamber is provided toward one end of the cover member 2000. Ideally, fluid flow port 2450 is filled from reservoir 2400 into which a volume of reagent may be dispensed e.g. by a fluid dispenser on a robotic head 4100. Ideally, reservoir 2400 has at least one inclined wall 2430 for guiding the reagent toward fluid flow port 2450 and into the reaction chamber.

Reagent may fill the reaction chamber by gravity filling from reservoir 2400. The level of fluid may be controlled hydrostatically e.g. when first fluid path 1500 is vented to atmosphere. This ensures reservoir 2400 contains enough reagent/wash solution to cover the sample on the substrate or, in the case of washing, ideally to fill the reaction chamber. Fluid may be held in reservoir 2400 for later release into the reaction chamber by closing the downstream fluid path anywhere after second fluid flow port 2500. This may be controlled by a valve (not shown).

Alternatively, pressure, for example positive pressure, may be applied by a probe on the robotic head 4100 at the reservoir 2400, or a positive or negative pressure may be applied at fluid flow port 2500 toward the opposite end of the cover member to draw fluid from the reservoir into and across the reaction chamber. A probe of the robotic head 4100 may couple with chamfered portion 2460 of the fluid flow port 2450 for injection of reagent into the reaction chamber. Operation of a probe and fluid management systems filling, agitating and evacuating fluid from the chamber via fluid flow port 1520 in the closure body 1100 and fluid flow port 2500 in the cover member 2000 is typically under the control of a controller 4400 which actively controls fluid movement within the instrument 4000. This leads to consistent reagent application and hence consistent staining during sample processing steps. Further, more consistent washing can be achieved between processing steps as well as washing of the cover member.

FIGS. 16 to 19 show another embodiment of a cover member 2000, which is adapted for sliding engagement with closure body 1100. Cover member 2000 has an enlarged reservoir 2400 capable holding a higher volume of reagent such that multiple aliquots may be dispensed under control of the controller 4400 to fill the reaction chamber formed between the cover member 2000 and the substrate 6000, without the robotic head returning to the assembly 1000 to deliver reagent. This frees the robot's availability for delivery of reagent to other assemblies inside the instrument 4000. Notch 2240 is also provided for engagement with a spring clip in the closure body 1100 (not shown).

A compressible member in the form of gasket 2200 is provided to form a seal around the reaction chamber formed by the void in under surface 2800 of the cover member 2000 and the mounting surface 1200 of, or the substrate 6000 when placed in, assembly 1000. It is to be understood, however, that in some embodiments, the void may be defined by the compressible member, without a contoured void formed in the underside 2800 of the cover member body.

The cover member body may be manufactured using any suitable process such as e.g. injection moulding, 3D printing or the like. Ideally, gasket 2200 is applied to cover member 2000 in a simple injection process wherein the cover member is placed in a mould and a fluid gasket material is added to the mould, flowing into slots and voids in the cover member. In some embodiments, one or more gasket channels or ruts may be provided on the cover member underside 2800 to guide flow of the fluid gasket material onto the cover member. Cavities and voids (and ruts and channels) not intended to be filled by the flowable gasket material may be temporarily masked or occupied by features of the mould to preclude filling during the gasket formation process.

Ideally, cover member 2000, is manufactured with wedge shaped slots or openings 2250. These are provided with the thicker portion of the slots 2250 opening into the cover member top side 2900 and the thinner portion of the slots 2250 opening into the cover member underside 2800 (although the slots need not extend all the way through the cover member). The fluid gasket material flows into the slots and, once set, anchors the gasket 2200 to the cover member 2000.

Fluoro-silicon, liquid silicon rubber and other such silicon/rubber compounds are considered suitable for the gasket because of the ability to deposit the compound in liquid form into a mould or die for forming the gasket on the cover member. Using this process, the fluid gasket material also can be made to form a through or "via" which extends from cover member underside 2800 where the gasket 2200 is formed, through and lining fluid flow channel 2500 and forming an O-ring or seal around opening 2500 on cover member top side 2900. This manufacturing approach, in which fluid gasket material is "grown" on and into contours of the cover member 2000 produces more consistent and effective retention between the gasket material and the cover member material without adhesive and with few manufacturing steps. Provision of a sealing O-ring around outlet port 2500 is an additional advantage.

In use, force distribution member 1400 applies a closing force through spacing member 2950 and gasket 2200 compresses to provide a sealing function. A substantially rigid end stop 2840 is provided on the cover member underside 2800 to limit the extent to which the gasket 2200 can be compressed when the assembly is closed. The end stop 2840 prevents over-compression and preserves the integrity of gasket 2200, particularly after multiple uses of the cover member 2000. Additionally, end stop 2840 helps to ensure reaction chamber uniformity, by controlling chamber volume. Although the end stop 2840 is shown as a rail extending along the long sides and one end of the cover member underside 2800, it is to be understood that the end stop may take many forms such as a ridge, teeth, bumps, tabs or other feature on the cover member underside that prevents over compression of the gasket.

Additionally, cover member 2000 in FIGS. 16 to 19 provide cavities 2860, 2870 in cover member underside 2800 to mitigate bubble formation during reagent propagation in the reaction chamber, and/or debris collection in the reaction chamber after evacuation. Cavity 2860 extends substantially across the width of the reaction chamber defined and is in fluid communication with fluid inlet 2450. Fluid dispensed into inlet 2450 (via reservoir 2400, when present), first fills cavity 2860 which is shaped to create an even fluid front for the reagent to propagate across the reaction chamber toward outlet 2500. In use, the fluid front propagates substantially orthogonally across the reaction chamber, reducing the likelihood of bubble formation and consequently, achieving more even staining of tissue samples.

Second cavity 2870 is positioned at the opposing end of the reaction chamber and is shaped to draw reagent from the fluid front before it reaches the opposing corners of the reaction chamber formed by the inner wall of gasket 2200 or other walls of the cover member underside 2800. Cavity 2870 is in fluid communication with outlet 2500 through which spent reagent is evacuated. Capturing reagent using cavity 2870 before it reaches the corners of the reaction chamber aids in fluid evacuation, reducing the likelihood of reagent carry over which can adversely affect subsequent treatment steps. Cavity 2870 also aids in removal of bubbles from the staining region, giving rise to more even staining. It is to be understood that the shape and contours of cavity 2870 are illustrative only, and that the reverse c-shaped cavity may extend further along the side walls of the reaction chamber.

In some instances, user error may lead to attempts to use instrument 4000 when a cover member has not been installed in the closure body 1100. To minimise the likelihood of this occurring, cover member 2000 may incorporate a feature that is readily visible to the human operator and/or recognisable by the instrument 4000 to ensure the presence of the cover member 2000 in the staining assembly 1000 prior to use. This feature may incorporate an optic, magnetic, radio frequency, infra-red, or other machine-readable element that can be adapted for automatic detection by the instrument. In an embodiment, the feature is detectable by a sensing device on the instrument prior to performing a processing run on samples in the instrument. This enables the instrument system to notify a user or enter an alarm state when it detects a cover member 2000 is not present in the assembly 1000. Alternatively/additionally, the instrument may automatically detect absence of a cover member if the probe travels beyond an expected coupling position when attempting to dispense reagent into a cover member.

In one embodiment, cover member 2000 may further encode information relevant to the usage of the cover member, including but not limited to, the history of the cover member including the number of times the cover member has been used in a staining assembly, the number of wash cycles the cover member 2000 has undergone or any other information that may be relevant to the useable life cycle of the cover member. A cover member having one or more orientation and functional features is described in U.S. provisional patent application 61/696,529 entitled "Cover Tile with Orientation Indicia" having a filing date of 4 Sep. 2012, the entire contents of which is hereby incorporated herein by reference.

Cover member 2000 is designed such that it may be easily manufactured by e.g. injection moulding or the like. Because of the tolerances built into the assembly and the force distribution achieved by the closure body 1100, the cover member 2000 need not be manufactured with a precisely flat first side 2800 as sealing with the substrate may still be achieved by exploiting compliance in the cover member and/or gasket material and applying a distributed closing force. In use, force distribution member 1400 achieves substantially even contact between cover member 2000 and the substrate such that there is minimal uncontrolled egress of fluid from the reaction chamber during a treatment step. Furthermore, the cover member 2000 requires modest material quantities for production since most of the device is thin walled. In the embodiment illustrated, thicker walls 2420 which consume more material, are located further from the void 2850 which forms the reaction chamber to minimise manufacturing defects arising from the injection moulding process.

In one embodiment, the cover member 2000 comprises a cavity such as an air cavity, or cavity filled with a gas, fluid or viscous compound. In an embodiment, the cavity provides a temperature regulating capacity, for example, thermosealing the cover member from the ambient environment. In an embodiment, the cavity may be utilized to maintain or vary the temperature of the cover member and/or the reaction chamber.

In a preferred embodiment, cover member 2000 is manufactured from material which is sufficiently compliant that even if the first side 2800 is not manufactured completely flat, it will still form a sealed reaction chamber with the substrate in the sample processing assembly. The cover member 2000 may be manufactured from any single material, or combination of materials suitable for use with reagents typically utilized in clinical laboratories, for example a histopathology laboratory. Suitable materials for producing cover member 2000 include, but are not limited to, hydrophobic materials and thermostable materials such as thermostable plastics. Some suitable materials include but are not limited to Polycarbonate, Polyoxymethylene (acetal), Polyether ether ketone (PEEK), polyethylenes including high density polyethylene (HDPE) and ultra-high molecular weight polyethylene (UHMW-PE), Teflons including Teflon PE, Polypropylenes such as Fluorinated ethylene propylene (FEP), Cyclic Olefin Copolymers or combinations thereof, to name a few.

In one embodiment, the cover member 2000 may be manufactured in two or more components. In one embodiment, the cover member 2000 may be manufactured by processes including, but not limited to, one or more of co-molding, over-molding, and hot foil stamping (including hot foil stamping of compliant seal and heat sealed lamination). In such an arrangement, the main body portion 2600 may be manufactured from a polycarbonate, polypropylene, FEP or COC. Where combined materials are used for the main body portion 2600, a substantial portion may comprise FEP whereas supporting portion/s may comprise polycarbonate. Alternatively, a substantial portion of main body 2600 may comprise polypropylene in combination with polycarbonate for supporting portions. Using hot foil stamping, at least part of the walls 2100 forming sealing surface 2150 may then be applied. Similarly, Heat-sealed laminate polypropylene may be applied to the main body portion 2600 on the second side 2900 to form the spacing member 2950 and/or fluoro-silicon may be applied to the main body portion on the first side 2800 to form a gasket 2200.

In an instrument containing multiple sample processing assemblies 1000, there may be dedicated scavenging valves devoted to each assembly to individually control e.g. application of a vacuum during a wash step to ensure most reagent particles are dislodged and withdrawn from the reaction chamber. Each scavenging valve may be connected via a waste management system to waste reservoir 4300 for disposal or recycling. Individual control of treatment and wash steps by the controller 4400 enables improved scheduling on board the instrument 4000 which improves instrument efficiency and cost effectiveness.

Cover member 2000 may be provided with notches 2230, 2235 which are shaped to cooperate with corresponding protrusions 1230, 1235 on the mounting surface 1200 such that when in use, the notch and protrusion guide the cover member 2000 into position in the assembly 1000 to form a reaction chamber. In this way, the protrusions 1230, 1235 are used to position a substrate in the assembly, as well as guiding the cover member into position over the substrate to minimise the effect of stacked tolerances.

In some embodiments, the cover member may have one or more biasing arms 2700, 2710 configured to abut a reference member 1700, 1710 on the closure body when in use, thereby urging the cover member toward a protrusions 1230, 1235 on the assembly during the final stages of closing, as the closure body approaches the mounting surface. This provides controlled and repeatable positioning of the cover member 2000 relative to the substrate beneath it. Alternatively/additionally, features for biasing and aligning the substrate and the cover member can be incorporated into the mounting surface 1200.

The cover member may also have a release member 2300 on the first side 2800 adjacent the void, to assist with separation of the cover member 2000 from the substrate when the sample processing assembly 1000 is opened at the conclusion of processing. The release member 2300 may be a sprung release member in the form of a curved tongue which is configured to aid separation of the cover member 2000 from a substrate by breaking surface tension arising from residual reagent in the reaction chamber. This helps to overcome the forces of stiction that may arise between the sample-carrying substrate and the cover member at the conclusion of a processing step. This feature is not essential, however and is omitted from the cover member 2000 shown in FIGS. 16 to 19. Separation of the cover member from the substrate after staining may alternatively/additionally be aided in some embodiments by application of a negative pressure (vacuum) at opening 1260 in mounting surface 1200 so that the substrate is at least momentarily held on the mounting surface by a suction/vacuum force. Alternatively/additionally, separation elements may be incorporated into the closure body 1100 to aid in separation of the cover member from the substrate when the assembly is opened.

In some embodiments, second side 2900 of cover member 2000 may also be provided with spacing member 2950 in the form of a ridge or wall. Spacing member 2950 is substantially aligned with sealing surface 2150 and helps to evenly distribute force from the biasing means 1300 and force distribution member 1400. Spacing member 2950 assists with controlling thermal losses from the reaction chamber during heating, as described below. Spacing member 2950 may also be contoured around mouth 2910. Here, compliant material helps form a gasket-like seal 2920 around the mouth 2910 through which fluid may be exchanged with the reaction chamber via fluid flow port 2500 which is supplied via first fluid path 1500 in the closure body 1100. Seal 2920 may be integral with the cover member material, or it may be non-integral and formed from more compliant material.

While a cover member 2000 is retained in the sample processing assembly 1000, a number of processing steps can be conducted. Between processing steps, the reaction chamber may be evacuated e.g. by applying a negative pressure via first fluid path 1500 to withdraw fluid. In some steps, it may be desirable to "wash" inside the reaction chamber using a cleaning solution including components such as e.g. water (including distilled, double distilled, deionized and other variations of water), detergents, salts, enzymes, oxidizers, disinfectants, surfactants, emulsifiers etc. Cleaning may be achieved with or without a sample-carrying substrate in the assembly. In the absence of a substrate, the cover member 2000 forms a wash chamber with the mounting surface 1200. In either case, wash fluid can be applied through reservoir 2400 or through the first fluid path 1500 which is coupled with a fluid flow port 2500 in the cover member 2000 via openings 1520 and 2910.

Complete washing of the cover member 2000 may take place between processing of distinct samples, when the substrate has been removed from the sample processing assembly. The effectiveness of washing may be enhanced by providing one or more recesses 1250 in the mounting surface 1200. Here, recess 1250 is arranged co-linearly with the internal walls 2100 of the cover member 2000 when retained by the closure body 1100 in a substantially closed position. FIG. 9 is a section view of the sample processing assembly 1000 with region A illustrating the location of recess 1250 with respect to the cover member 2000. An enlarged view of region A is provided in FIG. 9A. In one embodiment, force distribution member 1400 is floating (i.e. not rigidly affixed) with respect to closure body 1100. This allows movement of the force distribution member somewhat independently of the closure body 1100 and provides engagement of the cover member 2000 with mounting surface 1200 when a substrate is not loaded into the staining assembly.

Figure 9A:
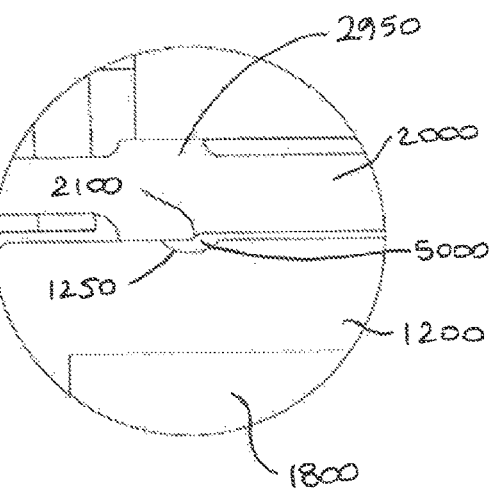

FIG. 9A shows internal wall 2100 of cover member 2000 positioned over recess 1250 in mounting surface 1200, and the formation of wash chamber 5000. As can be seen in FIG. 9A, the wash chamber 5000 is configured to facilitate washing of internal walls 2100 of the cover member 2000 so that there is minimal carryover of debris and/or build-up from processing steps performed during one assay, into a subsequent assay. Beneficially, complete washing of the cover member 2000 can be conducted while it is retained within the assembly, thereby eliminating manual washing. Wash reagent may be collected via an opening 1260 in the mounting surface, or via fluid flow ports 2450, 2500 in the cover member 2000.

Opening 1260 may be couplable with a second fluid flow path. The second fluid flow path (not shown) may facilitate fluid transfer between opening 1260 and a fluid source including a negative pressure source for draining reagent from the wash chamber 5000. Collected wash reagent may be redirected to a waste container/drain or for recycling. A vacuum may also be applied through opening 1260 to a substrate positioned on the mounting surface 1200 when in use, to assist in separation of the cover member 2000 from the substrate during initial opening of the assembly i.e. to overcome surface tension or stiction forces between the substrate and cover member.

As shown in FIGS. 1 to 4 and 9, a sample processing assembly 1000 according to an embodiment of the invention has a thermo module 1800 coupled with the mounting surface 1200. Thermo module 1800 is operable, preferably under control of a controller 4000, to vary the temperature within the reaction chamber. This is necessary for some processing steps and individual control of the thermo module, for heating and preferably cooling, gives rise to enhanced staining and improved scheduling capabilities on board an instrument 4000 in which there is a plurality of sample processing assemblies 1000 which each may be conducting entirely different sample processing assays.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present invention as defined in the claims appended hereto.

It is to be understood that the following claims are provided by way of example only. Features may be added to or omitted from the claims at a later date so as to further define or re-define the invention or inventions.

The invention claimed is:

1. A sample processing assembly for treatment of a sample on a substrate, the assembly comprising:
    a mounting surface for mounting the substrate;
    a cover member; and
    a closure body configured to releasably retain the cover member, the closure body being movable between a substantially closed position in which the cover member contacts the substrate and forms a reaction chamber therebetween, and an open position in which the cover member is removed from the substrate,
    wherein the cover member comprises a reservoir configured to receive and store a quantity of fluid and a fluid inlet port for ingress of the fluid from the reservoir into the reaction chamber, and
    wherein the cover member is releasably attached to the closure body while the closure body is disposed at the open position in which the cover member is removed from the substrate.

2. The assembly according to claim 1, including at least one first guide configured to limit movement of a substrate in at least a first direction during placement of the substrate in the assembly.

3. The assembly according to claim 2, wherein the at least one first guide is a protrusion on the mounting surface.

4. The assembly according to claim 1, further comprising closing biasing means for applying a biasing force such that the closure body is biased in the substantially closed position or an opening biasing means for applying an opening biasing force.

5. The assembly according to claim 4, further comprising a detention arm with a detent and a bearing surface disposed toward one end of the detention arm, such that when an opening force is applied to the bearing surface, the detent is released from the recess in the closure body and the closure body moves to the open position.

6. The assembly according to claim 1, further comprising a force distribution member for distributing a force applied to the closure body.

7. The assembly according to claim 1, wherein the closure body includes a first fluid flow path configured for fluid communication with a fluid port in a cover member when retained by the closure body, wherein in use the first flow path permits fluid transfer between the reaction chamber and a fluid source associated with the sample processing assembly.

8. The assembly according to claim 1, further comprising a thermo module coupled with the mounting surface, the thermo module being operable to vary the temperature within the reaction chamber.

9. The assembly according to claim 1, further comprising at least one recess in the mounting surface and arranged co-linearly with at least part of an interior wall of the cover member when retained by the closure body in a substantially closed position, the at least one recess facilitating cleaning of reagent from at least part of the cover member wall.

10. The assembly according to claim 1, wherein the cover member comprises a release member configured to bear against the substrate to assist with separation of the cover member from the substrate.

11. The assembly according to claim 1, wherein the reservoir is configured to receive and store a quantity of fluid sufficient for a plurality of treatment steps.

12. A cover member for use in a sample processing assembly, the cover member comprising:
    a first side;
    a second side opposing the first side;
    a void on a first side, the void forming a reaction chamber when the cover member contacts a substrate; and
    a compressible member on the first side configured to form a seal around the reaction chamber when in use, the compressible member material further extending around a fluid flow port in the cover member and comprising a sealing annulus around an opening of the fluid flow port on the cover member second side,
    wherein the cover member is releasably retained by a closure body of the sample processing assembly.

13. The cover member according to claim 12, further comprising a reservoir configured to receive and store a quantity of fluid sufficient for a plurality of treatment steps, and a fluid inlet port for ingress of fluid from the reservoir into the reaction chamber.

14. The cover member according to claim 12, further comprising a first cavity in the cover member first side which is in fluid communication with a fluid inlet, the first cavity being shaped to form a substantially orthogonal fluid front within the reaction chamber when in use.

15. The cover member according to claim 12, further comprising a second cavity in the cover member first side which is in fluid communication with a fluid outlet, the second cavity being shaped to draw fluid from a fluid front within the reaction chamber when in use, for evacuation through the fluid outlet.

16. A sample processing assembly for treatment of a sample on a substrate, the assembly comprising:
    a mounting surface for the substrate;
    a cover member;
    a closure body configured to releasably retain the cover member, the closure body being movable between a substantially closed position in which the cover member contacts the substrate and forms a reaction chamber therebetween, and an open position in which the cover member is removed from the substrate; and
    at least one first guide configured to limit movement of a substrate in at least a first direction during placement of the substrate in the assembly,
    wherein the at least one first guide is a protrusion on the mounting surface, and
    wherein the cover member includes a notch which accommodates the first guide when the closure body is in the substantially closed position.

17. The sample processing assembly according to claim 16, further comprising:
    biasing means for applying a biasing force such that the closure body is biased in the substantially closed position.

18. The sample processing assembly according to claim 16, wherein the cover member comprises a release member configured to bear against the substrate to assist with separation of the cover member from the substrate.

19. The sample processing assembly according to claim 16, wherein the cover member comprises a reservoir configured to receive and store a quantity of fluid sufficient for a plurality of treatment steps, and a fluid inlet port for ingress of fluid from the reservoir into the reaction chamber.

* * * * *